(12) United States Patent  (10) Patent No.: US 8,840,029 B2
Lawandy et al.  (45) Date of Patent: Sep. 23, 2014

(54) MULTI WAVELENGTH EXCITATION/EMISSION AUTHENTICATION AND DETECTION SCHEME

(75) Inventors: Nabil Lawandy, Saunderstown, RI (US); Andrei Smuk, Smithfield, RI (US); Leif Olson, Riverside, RI (US); Charles Zepp, Hardwick, MA (US)

(73) Assignee: Spectra Systems Corporation, Providence, RI (US)

( * ) Notice: Subject to any disclaimer, the term of this patent is extended or adjusted under 35 U.S.C. 154(b) by 251 days.

(21) Appl. No.: 13/352,953

(22) Filed: Jan. 18, 2012

(65) Prior Publication Data

US 2013/0182241 A1   Jul. 18, 2013

(51) Int. Cl.
*G06K 19/06* (2006.01)

(52) U.S. Cl.
USPC .......................................... 235/491; 235/375

(58) Field of Classification Search
USPC ......................... 235/491, 375, 468, 487, 454
See application file for complete search history.

(56) References Cited

U.S. PATENT DOCUMENTS

| | | | |
|---|---|---|---|
| 7,355,944 B2 * | 4/2008 | van de Grampel et al. | 369/53.1 |
| 7,667,828 B2 * | 2/2010 | Gibson | 356/71 |
| 2005/0236481 A1 * | 10/2005 | Gascoyne et al. | 235/454 |
| 2006/0219791 A1 * | 10/2006 | Mossberg et al. | 235/454 |
| 2009/0033932 A1 * | 2/2009 | Gibson | 356/326 |
| 2011/0108739 A1 * | 5/2011 | Hanko | 250/459.1 |

* cited by examiner

*Primary Examiner* — Edwyn Labaze
(74) *Attorney, Agent, or Firm* — Barlow, Josephs & Holmes, Ltd.

(57) ABSTRACT

A system and method for authentication of secure products is disclosed. The security feature contains a first component in the form of an emitter capable of emitting light in response to external pump light. The security feature also contains a second component in the form of a taggant that absorbs light in a spectrally narrow range compared to the broader excitation spectrum of the first material. In this manner the emitter and taggant work in combination with one another to create an emission response significantly dependent on the illumination wavelengths and unique to the specific combination of the components. The emitter and taggant can be in the form of a mixture. Further the emitter and taggant may be applied in close proximity to one another, such as within two separate coating layers on a suitable substrate.

19 Claims, 4 Drawing Sheets

MULTI WAVELENGTH EXCITATION/EMISSION AUTHENTICATION AND DETECTION SCHEME

BACKGROUND OF THE INVENTION

The present invention relates generally to detectable security markings. More specifically, the present invention relates to optically encoded phosphorescent and fluorescent security markings that range in wavelength from the ultraviolet to the far infrared spectral regions.

Counterfeiting and forgery have become significant concerns in the modern economy and marketplace. While fraudulent activities such as counterfeiting currency and forging signatures or handwriting are common, methods of creating and perfecting forgeries and counterfeit documents have become easier and more available with the advent of highly skilled computer printing and processing. Given the advances and reduction in cost of computing technology and printing techniques, the incidence of forgeries, counterfeited documents, and other fraudulent activities have increased. This is problematic in that countless areas of today's high-technology society require and rely upon certification, authentication and protection of highly valuable documents, papers, currency or other materials in order to prevent fraud and counterfeiting. In an attempt to combat the use of counterfeit money, for example, the United States Treasury, as far back as 1991, has continually added security safeguard features to the various denominations of currency. These safeguards have included watermarks, security threads embedding in the paper, microprinting, color-shifting ink, and the use of multicolored bills.

Generally, current methods of authentication of currency involve visual observation scanning under ultraviolet lamps notes containing security threads and emissive materials such as inks and planchettes. Such security threads emit a distinct marking, color or code in response to exposure to the ultraviolet light. In some circumstances, the emissive features of different denominations of notes can emit different colors. In addition to the colors of the emission, a code number or other unique identifier can be detected by the naked eye when the note is exposed to ultraviolet light or excitation of some form.

In addition to protecting against counterfeit currency, authentication of valuable documents or materials also affects many facets of the economy. For example, notaries public use a raised stamp to authenticate notarized documents; drivers' licenses, passports and other photographic identification contain holograms and microprinting; sporting memorabilia and retail clothiers use holographic tags and stamps to prove authenticity. Even fashion designers are now including authentication devices in their clothing to prevent passing off of knock-offs as designer products.

A disadvantage to these traditional security features is that they are visible and known to the world. If a counterfeiter is aware there is a security thread in a bill or a watermark in a document, replication of the security feature is easier. Once a feature is made known to the public, a counterfeiter may begin to develop specific strategies and solutions to overcome the security protections provided by the specific feature.

Accordingly there is a need for a covert security marking to be incorporated into currency, important and valuable documents, packaging, and other authentic materials to prevent unauthorized copying, forging, counterfeiting and other fraudulent use.

BRIEF SUMMARY OF THE INVENTION

In this regard, the present invention provides embodiments of systems and methods for document and product authentication using a combination of interacting absorption and emission signatures. Such of the signatures are provided in the form of florescent or phosphorescent coatings, inks, security threads, planchettes, particles and/or substrates. The various embodiments of the present invention are used for authentication and protection of items, including solids and liquids and particularly secure documents including banknotes, ID documents, Visas, and tax stamps. The system is comprised of a first emitter material in combination with an absorptive authentication device or taggant. The technology can also be used to authenticate liquids such as fuels, perfumes and pharmaceuticals wherein the authentication device is dissolved therein.

Absorptive inks, coatings and substrates in combination with an authentication device and may also be utilized for creating unique optical signatures for authentication and coding. Such signatures are created using a variety of materials including, for example, dyes, quantum dots, semiconductors, and nanostructures with plasmon-polariton resonances. Both emissive and absorptive features are utilized across the electromagnetic spectrum spanning from the ultraviolet spectrum to the infrared ("IR") spectrum. Spectrally overlapping combinations of such features are used to create codes that are covert to the naked eye and signatures through a variety of application methods to imprint articles with such protective measures.

It is therefore an object of the present invention to provide a covert security marking to be incorporated into currency, important and valuable documents, packaging, and other authentic materials to prevent unauthorized copying, forging, counterfeiting and other fraudulent use. It is a further object of the present invention to provide a covert security marking comprised of an emitter that is capable of emitting light in response to an external light pump and a taggant that absorbs light in a narrow spectral range. Still further the disclosure provides for an automated detection system employing two pump sources at different wavelengths to detect a differential illumination response that indicates whether a taggant is present within an emitter material.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention.

DETAILED DESCRIPTION OF THE INVENTION

Figure 1:
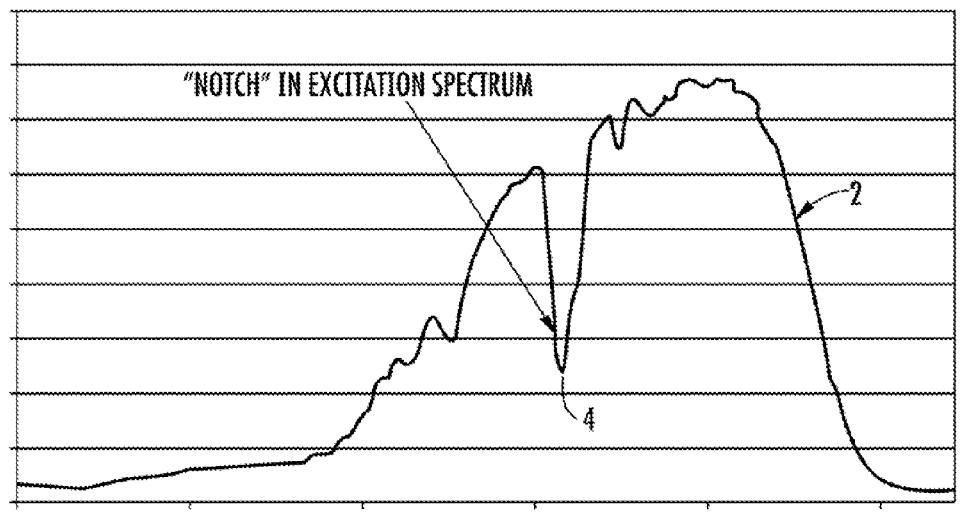
FIG. 1 is an illustrative graph of the spectral excitation of an enhanced security feature in accordance with an embodiment of the invention.

The invention will be more completely understood through the following detailed description, which should be read in conjunction with the attached drawings. While detailed embodiments of the invention are disclosed herein, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the invention in virtually any appropriately detailed embodiment.

Most generally, embodiments of the invention include florescent or phosphorescent illuminations in response to a targeted emission which are combined with a narrow band absorption (narrower than the excitable emission bandwidth) material (hereinafter taggant) to create a new type of authentication and coding signature. A broad-band emissive material is combined with one or more a narrow-band absorptive taggants having a narrower absorption bandwidth than the emission line to create an emissive signature with one or more specific dips or notches at specific excitation wavelengths. Through the system the emitter/taggant combination can be non-concurrently subjected to irradiation at two different wavelengths in a manner that it is evident that when the taggant is present the illumination at one of the irradiation wavelengths has been attenuated as will be described in more detail below. Through this combination, a signature with at least one or more dips or features at given wavelengths may be created when using more than one unique taggant component under the emissive line. Authentication signatures or codes which depend on the spectral positions, shapes, irradiation wavelengths and notch depth ratios can be created. Codes or signatures using several combined emissive materials to create a broad emission that overlaps the absorption lines are also possible.

The disclosed authentication system is intended for authentication of products, including solids and liquids and particularly secure documents including banknotes, ID documents, Visas, and tax stamps. The system is comprised of the material imbedded in the product or banknotes (the substrate, coating, printing ink or varnish, etc) and the authentication device. The technology can also be used to authenticate liquids such as fuels, perfumes and pharmaceuticals with a dissolved material.

The security device generally contains a first component in the form of an emitter. The emitter is either a fluorescent or phosphorescent material capable of emitting light in response to external pump light. The spectral range of the external pump light that is able to induce emission of light in the emitter comprises the excitation spectrum of the emitter. The security device also generally contains a second component in the form of a taggant that absorbs light in a spectrally narrow range compared to the broader excitation spectrum of the emitter. In this manner the emitter and taggant work in combination with one another to create a spectral signature that is detectable when irritated at a specific wavelength or at more than one targeted wavelength range.

In an embodiment the present invention provides a method of authenticating an article comprising providing an emitter substance capable of emitting light in response to an illumination by any wavelength selected from a broad spectral range, said range referred to as excitation spectrum; providing a taggant substance capable of absorbing light in at least one narrow spectral range absorption within the excitation spectrum; and non-concurrently exciting said emitter and taggant substances with at least two spectrally distinctive illuminations selected within said broad excitation spectrum, a first illumination spectrally corresponding to said one narrow absorption range of the taggant and a second illumination spectrally falling outside said one narrow absorption range of the taggant. The method may further include detecting the emission resulting from the first and second illuminations of the combined substances; and comparing a relative level of the detected emissions to determine whether said taggant is present.

The emitter and taggant can be in the form of a mixture. Further the emitter and taggant may be applied in close proximity to one another, such as within two separate coating layers on a suitable substrate. Materials suitable for use as an emitter can be any fluorescent or phosphorescent material, either Stokes or anti-Stokes shifting and may further include fluorescent dyes, phosphors including storage phosphors, organic or inorganic pigments, metal chelates, semiconductor quantum dots or up-converting materials. Materials suitable for use as a taggant can be any material with sufficiently spectrally narrow absorption, including but not limited to organic dyes of the cyanine, phthalocyanine or squaraine type, or inorganic pigments and absorbers such as but not limited to rare earths.

In the context of the present invention specific pairs of emitter and taggant materials are chosen such that the absorption spectrum of the taggant falls within the range of the excitation spectrum of the emitter. As is illustrated at FIG. 1, when the excitation spectrum 2 of such a mixture or layer construction is measured with a fluorimeter, a "notch" 4 in that spectrum will be evident, caused by the absorbance of the taggant. It is of note that if such a mixture is non-concurrently irradiated at two wavelengths, a first one using pump that corresponds to the absorbance "notch" wavelength of the taggant and a second using a second pump that corresponds to a wavelength that falls outside the absorbance "notch" wavelength, it will be evident that the intensity of the illumination emission as a result from the irradiation by the first pump has been attenuated by the absorbance of the taggant. The ratio of the differences in the emission caused by non-concurrent irradiation of the two pumps at these two wavelengths becomes a measure of the presence or the amount of the taggant within the security feature. It is this ratio that can be used as a means to uniquely mark an object.

Figure 2:
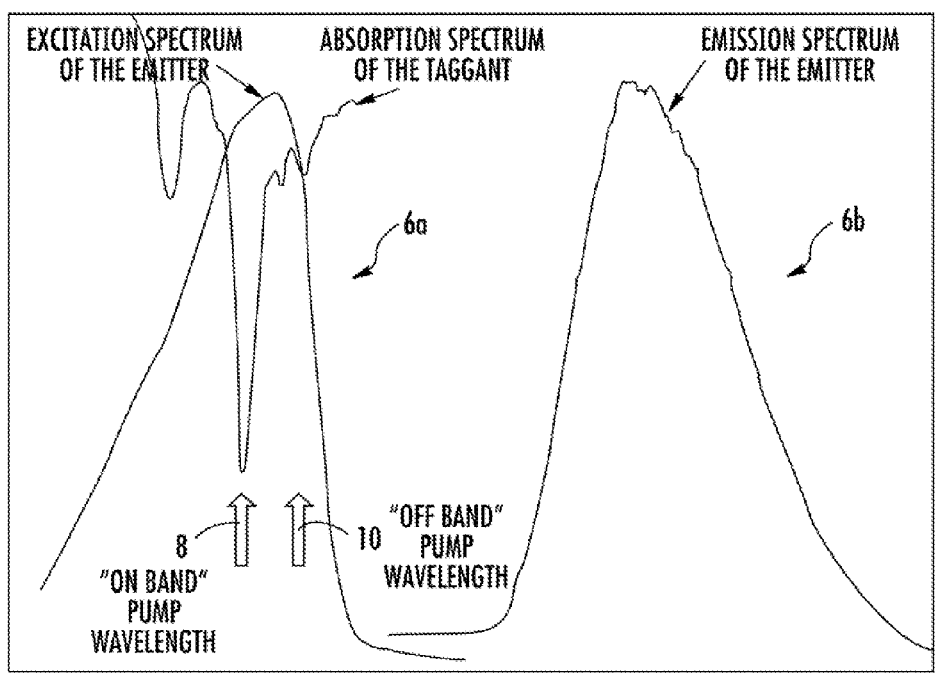
FIG. 2 is an illustrative graph of the spectral excitation, absorption and emission of an enhanced security feature in accordance with an embodiment of the invention.

As is illustrated in the excitation spectrum depicted at FIG. 2, in its simplest embodiment, the authentication method is based on non-concurrently illuminating the emitter using a pair of spectrally narrow pumps, such as for example, laser diodes. The curve 6a on the left is the result of modulated excitation when a taggant is present and the curve 6b on the right is the result when no taggant is present. One of the pumps 8 is coincident with the absorption band of the taggant, shown as the on-band pump in FIG. 2. The second pump 10 is at a wavelength that is essentially not overlapping with the absorption band of the taggant, shown as the off-band pump in FIG. 2. The illumination resulting from non-concurrent excitation of the two pumps is collected and sent to a detector, which in turn generates signal. As can be seen in the illumination curve 6b depicted at the right in FIG. 2, without the taggant present, both pumps excite certain reference amounts of illumination that in turn indicates presence of the emitter and absence of the taggant. When the taggant is present within the security feature, as depicted in the illumination curve at the left in FIG. 2, the on-band pump that is coincident with the absorption wavelength of the taggant is partially absorbed by the taggant, therefore exciting less light in the emitter compared to the reference amount. The off-band pump in this case still generates the same amount of light as its reference. The combined spectral emission and attenuation resulting from the combination of the on-band and off-band pumps thus indicates the presence of the emitter and taggant combination within the security feature.

One advantage of the authentication method of the present invention is simplicity and low cost of the optical instrumentation required to perform the analysis. Instead of a costly spectrometer and data analysis of the curve shape, the scheme requires two monochromatic pumps or light sources and a means for taking a measurement of the resulting emitted light intensity. It is of note that while simplicity and low cost has been emphasized, within the disclosure of the present invention it is also possible to perform a more sophisticated detection scheme using this method. Such a scheme would involve three or more pumps, spectrally positioned on and around the absorption band of the taggant to provide more detailed excitation information specific to the location of the absorption band of the taggant. Similarly, more than one taggant may be used to create a plurality of absorption notches.

Figure 3:
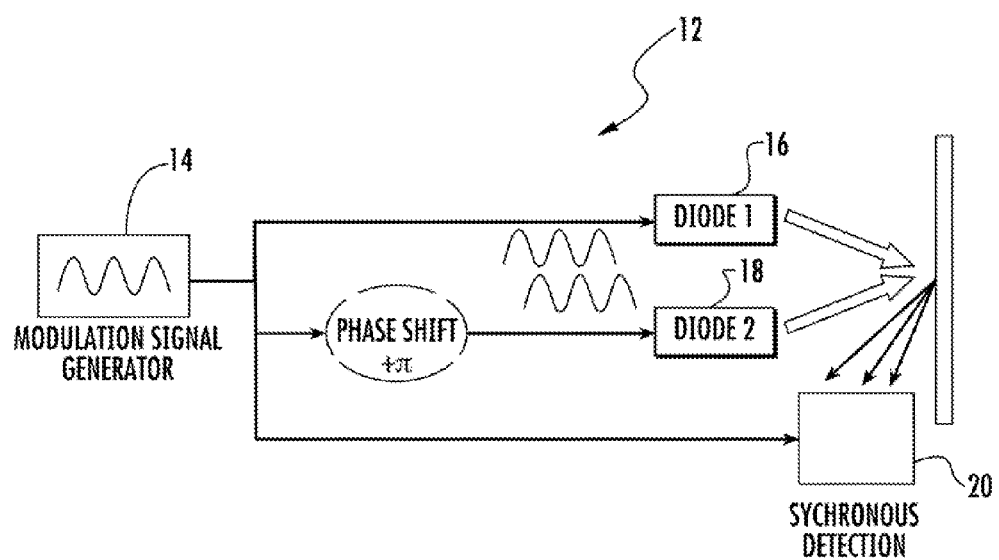
FIG. 3 is a schematic diagram of a system for detecting an enhanced security feature in accordance with the present invention.

In accordance with the teachings of the present invention a detection system 12 operating in accordance with the principle described above is depicted at FIG. 3. The detection system 12 allows high sensitivity implementations, including but not limited to phase detection, or synchronous detection. The schematic depicted at FIG. 3 shows a possible detection scheme with high signal-to-noise ratio. A signal generator 14 provides a modulated driver signal to energize pumps in the form of diodes 16, 18. In this arrangement the modulated drive signal is phase shifted in order to alternately drive laser diode 16 and laser diode 18, one of which operates at the on-band wavelength, the other one at the off-band wavelength. The light emissions induced in the sample by the two coincident laser diode beams is collected by the detector 20 to generate electrical signal at the modulation frequency, which is synchronously detected. The detected signals are compared to one another. In the absence of the taggant within the security feature the detected signals from individual diodes when compared to one another are balanced and thus generate zero signal at the modulation frequency. With the taggant present, the balance of the compared signals is shifted towards the off-band diode pump signal that results in a non-zero signal at the modulation frequency.

Figure 4:
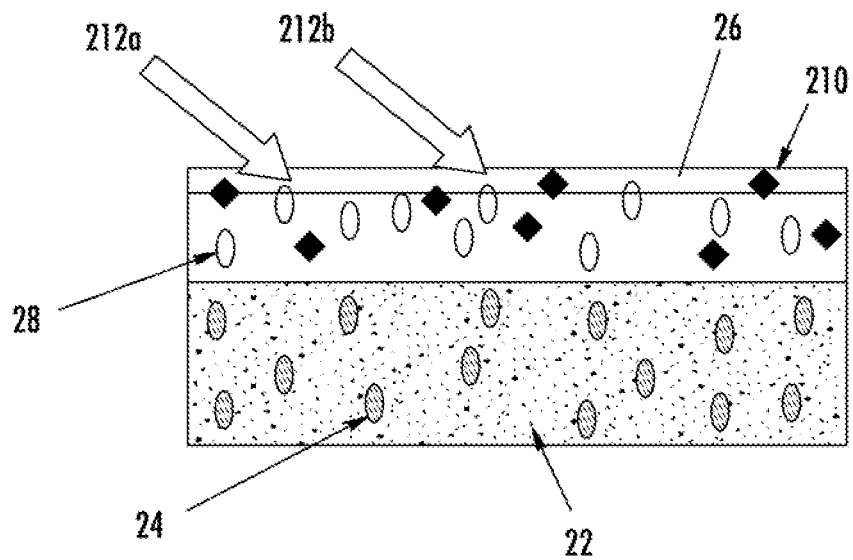
FIG. 4 is a cross-section of a coating which is deposited above an emitting and absorbing substrate in accordance with an embodiment of the invention.

In one illustrative embodiment of the present invention as depicted at FIG. 4, a substrate 22 material of paper or plastic is embedded with one or more taggant materials 24 that have specific wavelength absorption characteristics. An ink or dye coating 26 is embedded with one or more emitters 28, 210. The ink or dye coating 26 is deposited on the substrate 22 in proximity to the absorbing materials to form the security feature. When narrow band energy is applied to the security feature using an on-band pump 212a and off-band pump 212b the ratio of the detected emissions generated by the alternating on-band and off-band pump energy yields verification as to the presence or lack of taggant.

Figure 5:
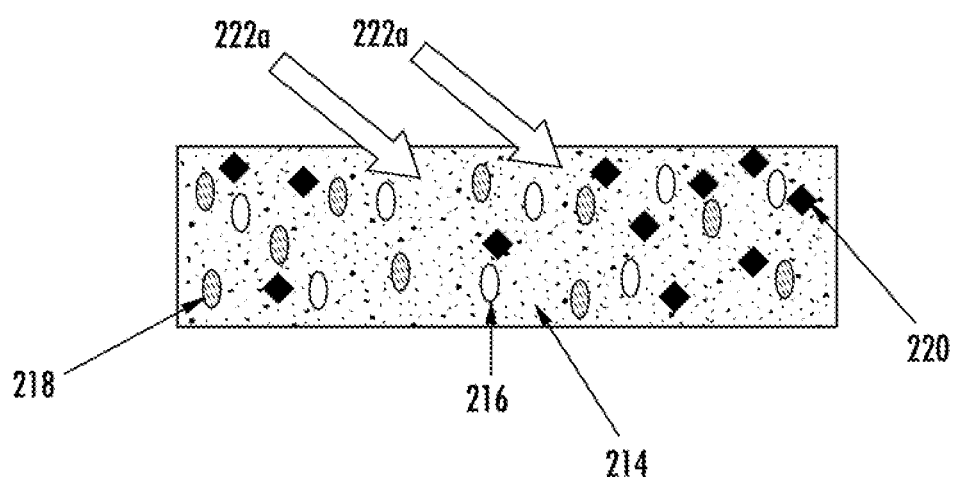
FIG. 5 is a cross-section of a security feature dispersed within a fluid, coating or ink in accordance with an embodiment of the invention.

In another embodiment as depicted at FIG. 5, the at least one taggant and the at least one emitter material can be combined in one layer as a coating or ink or dispersed within a fluid material such as a fuel, perfume or pharmaceutical. As shown schematically in FIG. 2, a host material 214, includes therein emitter particles 216 and taggant particles 218. When narrow band energy is applied to the host material containing the security feature using an on-band pump 222a and off-band pump 222b the ratio of the detected emissions generated by the alternating on-band and off-band pump energy yields verification as to the presence or lack of taggant. According to one embodiment, the coating or fluid may be an ink for use in a variety of ink based printing techniques, such as, without limitation, Intaglio and lithographic print.

According to one embodiment of the invention, a machine-readable, covert security feature is included for use in security threads in a currency note or other valuable document. A covert security feature may be embedded within the security thread or planchette, resulting in no apparent visible change of the excited signature of the threads when viewed using a standard ultraviolet source or lamp or other appropriate excitation source. The covert security feature, while undetectable to the naked eye, conforms to the teachings of the present invention in that when narrow band energy is applied to the host material containing the security feature using an on-band and off-band pump, the ratio of the detected emissions generated by the alternating on-band and off-band pump energy yields verification as to the presence or lack of taggant. The incorporation of the new machine readable, covert feature is implemented without any change to the public perception of the excited emission signature, thereby making forgery or duplication of the material more difficult.

In one embodiment the security feature comprises an emitter substance capable of emitting light in response to an illumination by any wavelength selected from a broad spectral range, said range referred to as excitation spectrum; at least one taggant substance capable of absorbing at least one spectrally narrow range within said excitation spectrum, wherein the emitter substance and the taggant substance respond to at least two illuminations within said broad excitation spectrum, a first illumination spectrally corresponding to said one narrow absorption range of the taggant and a second illumination spectrally falling outside said one narrow absorption range of the taggant to determine whether said taggant is present.

While embodiments of the invention described herein show and describe single spectral notches, one skilled in the art should recognize that any number of spectral characteristics may be incorporated into a security feature without deviating from the scope of the invention. For example, one or more types of emitter particles or taggant particles may be incorporated into the security feature to provide a series of notches or other distinguishable characteristics.

Further, while embodiments of the invention described herein discuss the comparison of excitation generated by two or three emitters, one skilled in the art should recognize that the covert distinguishable characteristics of the security feature are not limited to a single notch detection. For example, a security feature may contain multiple taggants with absorption notches in other or multiple spectral ranges ranging from the ultraviolet to the far infrared range.

While the invention has been described with reference to illustrative embodiments, it will be understood by those skilled in the art that various other changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed:

1. A method of authenticating an article comprising;
   providing an emitter substance that emits light in response to an illumination by any wavelength selected from a broad spectral range, said range referred to as excitation spectrum;
   providing a taggant substance that absorbs light in at least one narrow spectral range absorption within the excitation spectrum; and
   non-concurrently exciting said emitter and taggant substances with at least two spectrally distinctive illuminations selected within said broad excitation spectrum, a first illumination spectrally corresponding to said one narrow absorption range of the taggant and a second illumination spectrally falling outside said one narrow absorption range of the taggant.

2. The method of claim 1, further comprising:
   detecting the emission resulting from the first and second illuminations of the combined substances; and
   comparing a relative level of the detected emissions to determine whether said taggant is present.

3. The method of claim 1, further comprising:
   disposing the taggant substance in a substrate.

4. The method of claim 3, further comprising:
   disposing the emitter substance in a coating on the substrate.

5. The method of claim 1, further comprising:
   disposing the taggant substance and the emitter substance in a coating on a substrate.

6. The method of claim 1, further comprising:
   disposing the taggant substance and the emitter substance within a fluid.

7. The method of claim 1, further comprising:
   disposing the taggant substance and emitter substance on a security thread.

8. The method of claim 1, wherein the first and second illuminations are produced by one or more laser diodes.

9. The method of claim 1, wherein the first and second illuminations are phase shifted relative to one another.

10. The method of claim 9, further comprising:
    detecting a corresponding light emission caused by said first and second illuminations.

11. The method of claim 1, wherein the illuminations are spectrally within the group consisting of the visible band, ultraviolet band and the infrared band.

12. A security feature comprising:
    an emitter substance that emits light in response to an illumination by any wavelength selected from a broad spectral range, said range referred to as excitation spectrum; and
    at least one taggant substance that absorbs at least one spectrally narrow range within said excitation spectrum;
    wherein the emitter substance and the taggant substance respond to at least two illuminations within said broad excitation spectrum, a first illumination spectrally corresponding to said one narrow absorption range of the taggant and a second illumination spectrally falling outside said one narrow absorption range of the taggant to determine whether said taggant is present.

13. The security feature of claim 12, further comprising:
    disposing the taggant substance in a substrate.

14. The security feature of claim 13, further comprising:
    disposing the emitter substance in a coating on the substrate.

15. The security feature of claim 12, further comprising:
    disposing the taggant substance and the emitter substance in a coating on a substrate.

16. The security feature of claim 12, further comprising:
    disposing the taggant substance and the emitter substance within a fluid.

17. The security feature of claim 12, further comprising:
    disposing the taggant substances and emitter substance on a security thread.

18. The security feature of claim 12, wherein a light emission produced by said taggant and emitter combination is different in response to said first and second illuminations.

19. The security feature of claim 18, wherein said difference in response can be detected and compared to determine the presence of said taggant within said security feature.

* * * * *